US012308127B2

(12) United States Patent
Gooßen et al.

(10) Patent No.: US 12,308,127 B2
(45) Date of Patent: May 20, 2025

(54) GUIDED REVIEWS OF PRIOR EXAMS AND REPORTS

(71) Applicant: KONINKLIJKE PHILIPS N.V., Eindhoven (NL)

(72) Inventors: André Gooßen, Radbruch (DE); Axel Saalbach, Hamburg (DE); Rafael Wiemker, Kisdorf (DE); Tim Philipp Harder, Ahrensburg (DE); Tom Brosch, Hamburg (DE); Hrishikesh Narayanrao Deshpande, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 304 days.

(21) Appl. No.: 17/074,669

(22) Filed: Oct. 20, 2020

(65) Prior Publication Data
US 2021/0134465 A1   May 6, 2021

(30) Foreign Application Priority Data
Nov. 4, 2019  (EP) ..................... 19206904

(51) Int. Cl.
*G16H 50/70* (2018.01)
*A61B 6/00* (2006.01)
(Continued)

(52) U.S. Cl.
CPC ........... *G16H 50/70* (2018.01); *A61B 6/5217* (2013.01); *G06F 40/253* (2020.01); *G06N 20/00* (2019.01);
(Continued)

(58) Field of Classification Search
CPC ..... G06F 40/253; A61B 6/5217; G06N 20/00; G06T 2200/24; G06T 2207/30004;
(Continued)

(56) References Cited

U.S. PATENT DOCUMENTS

2016/0203263 A1* 7/2016 Maier ................... G16H 30/40
                                                            705/2
2016/0267222 A1   9/2016 Larcom
(Continued)

FOREIGN PATENT DOCUMENTS

WO   2017151757   9/2017

OTHER PUBLICATIONS

Shin, et al: "Increased risk of refractory Mycoplasma pneumoniae pneumonia in children with atopic sensitization and asthma", Korean J Pediatr. Jun. 2014; 57(6): 271-277.
(Continued)

*Primary Examiner* — Manuchehr Rahmjoo (57) ABSTRACT

A system for reviewing a prior medical image and a related prior medical report, including: a plurality of measurement tools configured to: receive an input medical image and information regarding a medical finding; analyze the input medical image to determine a measurement relating to the medical finding; and output the measurement relating to the medical finding; a report analyzer configured to: receive the prior medical report; analyze the prior medical report to extract first information regarding a first medical finding described in the medical report; select a first measurement tool of the plurality of measurement tools to analyze the prior medical image based upon the first extracted information; and output the first extracted information to the first measurement tool, wherein the first measurement tool analyzes the prior medical image to produce a first updated measurement of the first medical finding and the first measurement tool analyzes a new medical image associated with the prior medical image to produce a new first measurement of the first medical finding; a report generator configured to receive the new first measurement and to produce a new report based upon the new first measurement.

20 Claims, 4 Drawing Sheets

(51) Int. Cl.
  *G06F 40/253* (2020.01)
  *G06N 20/00* (2019.01)
  *G06T 7/00* (2017.01)
  *G06T 7/62* (2017.01)
  *G16H 15/00* (2018.01)
  *G16H 30/20* (2018.01)

(52) U.S. Cl.
  CPC .............. *G06T 7/0014* (2013.01); *G06T 7/62* (2017.01); *G16H 15/00* (2018.01); *G16H 30/20* (2018.01); *G06T 2200/24* (2013.01); *G06T 2207/30096* (2013.01)

(58) Field of Classification Search
  CPC ......... G06T 2207/30096; G06T 7/0014; G06T 7/0016; G06T 7/62; G16H 10/60; G16H 15/00; G16H 30/20; G16H 50/70
  See application file for complete search history.

(56) References Cited

U.S. PATENT DOCUMENTS

| | | |
|---|---|---|
| 2016/0361025 A1 | 12/2016 | Reicher |
| 2018/0060535 A1* | 3/2018 | Reicher ............... G16H 50/30 |
| 2018/0137244 A1 | 5/2018 | Sorenson |
| 2018/0341751 A1 | 11/2018 | Lyman |

OTHER PUBLICATIONS

Kohli, et al: Indiana University Chest X-ray Collection, 2013 https://openi.nlm.nih.gov/detailedresult?img=CXR111_IM-0076-1001&query=&req=4.

* cited by examiner

GUIDED REVIEWS OF PRIOR EXAMS AND REPORTS

CROSS REFERENCE TO RELATED APPLICATIONS

This application claims the benefit of European Patent Application Number 19206904.5 filed Nov. 4, 2019. This application is hereby incorporated by reference herein.

FIELD OF THE INVENTION

Various exemplary embodiments disclosed herein relate generally to a system and methods for guided reviews of prior exams and reports.

BACKGROUND OF THE INVENTION

In a follow-up examination, a radiologist typically starts with an assessment of the prior report. If it contains relevant measurements (such as a tumor diameter), the radiologist will usually open the original image in order to confirm the measurement. Measurements are typically associated with a high degree of uncertainty, resulting from differences in clinical guidelines, employed computer-aided diagnosis (CAD) solution or personal style of the radiologist. Therefore, the radiologist could come up with different estimates, leading to erroneous estimates of the disease progression, and finally resulting in severe consequences in the treatment of the patient.

SUMMARY OF THE INVENTION

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a system for reviewing a prior medical image and a related prior medical report, including: a plurality of measurement tools configured to: receive an input medical image and information regarding a medical finding; analyze the input medical image to determine a measurement relating to the medical finding; and output the measurement relating to the medical finding; a report analyzer configured to: receive the prior medical report; analyze the prior medical report to extract first information regarding a first medical finding described in the medical report; select a first measurement tool of the plurality of measurement tools to analyze the prior medical image based upon the first extracted information; and output the first extracted information to the first measurement tool, wherein the first measurement tool analyzes the prior medical image to produce a first updated measurement of the first medical finding and the first measurement tool analyzes a new medical image associated with the prior medical image to produce a new first measurement of the first medical finding; a report generator configured to receive the new first measurement and to produce a new report based upon the new first measurement.

Various embodiments are described, further including: a graphical user interface configured to display the prior image and new image.

Various embodiments are described, further including: a graphical user interface configured to display one or more of first updated measurement, new first measurement, condition progression information, prior report, and new report.

Various embodiments are described, wherein the report analyzer includes a natural language processing engine.

Various embodiments are described, wherein the report generator includes a natural language processing engine.

Various embodiments are described, wherein the report generator further receives style information from the report analyzer and the new report has the same style as the prior report.

Various embodiments are described, wherein the report analyzer is further configured to: analyze the prior medical report to extract second information regarding a first medical finding described in the medical report; select a second measurement tool of the plurality of measurement tools to analyze the prior medical image based upon the second extracted information; and output the second extracted information to the second measurement tool, wherein the second measurement tool analyzes the prior medical image to produce a updated second measurement of the first medical finding and the second measurement tool analyzes a new medical image associated with the prior medical image to produce a new second measurement of the first medical finding.

Various embodiments are described, wherein the report analyzer is further configured to: analyze the prior medical report to extract second information regarding a second medical finding described in the medical report; select a second measurement tool of the plurality of measurement tools to use to analyze the prior medical image based upon the extracted second information; and output the second extracted information to the second measurement tool, wherein the second measurement tool analyzes the prior medical image to produce an updated second measurement of the second medical finding and the second measurement tool analyzes a new medical image associated with the prior medical image to produce a new first measurement of the second medical finding.

Various embodiments are described, wherein the first measurement tool automatically analyzes the medical image to determine a measurement relating to the medical finding.

Various embodiments are described, wherein the first measurement tool receives user input to analyze the medical image to determine a measurement relating to the medical finding.

Various embodiments are described, wherein the first measurement tool uses one of machine learning and image processing to analyze the medical image.

Further various embodiments relate to a method for reviewing a prior medical image and a related prior medical report, including: receiving, by a report analyzer, the prior medical report; analyzing, by the report analyzer, the prior medical report to extract first information regarding a first medical finding described in the medical report; selecting a first measurement tool of a plurality of measurement tools to analyze the prior medical image based upon the first extracted information; outputting the first extracted information to the first measurement tool; analyzing, by the first measurement tool, the prior medical image to produce a first updated measurement of the first medical finding; analyzing, by the first measurement tool, a new medical image associated with the prior medical image to produce a new first measurement of the first medical finding; outputting, by the first measurement tool, the new first measurement relating to the medical finding to a report generator; and producing, by the report generator, a new report based upon the new first measurement.

Various embodiments are described, further including displaying, by a graphical user interface, the prior image and new image.

Various embodiments are described, further including displaying, by a graphical user interface, one or more of first updated measurement, new first measurement, condition progression information, prior report, and new report.

Various embodiments are described, wherein the report analyzer is a natural language processing engine.

Various embodiments are described, wherein the report generator is a natural language processing engine.

Various embodiments are described, wherein the report generator further receives style information from the report analyzer and the new report has the same style as the prior report.

Various embodiments are described, further including, analyzing, by the report analyzer, the prior medical report to extract second information regarding a first medical finding described in the medical report; selecting a second measurement tool of the plurality of measurement tools to analyze the prior medical image based upon the second extracted information; outputting the second extracted information to the second measurement tool; analyzing, by the second measurement, the prior medical image to produce a updated second measurement of the first medical finding; and analyzing, by the second measurement, a new medical image associated with the prior medical image to produce a new second measurement of the first medical finding.

Various embodiments are described, further including, analyzing, by the second measurement, the prior medical report to extract second information regarding a second medical finding described in the medical report; selecting a second measurement tool of the plurality of measurement tools to use to analyze the prior medical image based upon the extracted second information; outputting the second extracted information to the second measurement tool, analyzing, by the second measurement tool, the prior medical image to produce an updated second measurement of the second medical finding; and analyzing, by the second measurement tool, a new medical image associated with the prior medical image to produce a new first measurement of the second medical finding.

Various embodiments are described, wherein the first measurement tool automatically analyzes the medical image to determine a measurement relating to the medical finding.

Various embodiments are described, wherein the first measurement tool receives user input to analyze the medical image to determine a measurement relating to the medical finding.

Various embodiments are described, wherein the first measurement tool uses one of machine learning and image processing to analyze the medical image.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION OF EMBODIMENTS

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

An important step in the reading of medical images is the review of prior images and their corresponding reports. In particular, in situations where quantitative information, e.g., size measurements such as the size of a tumor, are relevant. Due to differences in clinical guidelines employed, computer-aided diagnosis (CAD) solution, or personal style, the radiologist could come to contradicting measurements and erroneous findings, e.g., with respect to the progression of tumor growth.

The confirmation of a measurement involves multiple time-consuming and error-prone steps. Within a multi-image exam, the radiologist has to identify the referenced image from the exam. Thereafter the radiologist has to localize the described finding and re-execute the previous measurement. The findings may be the indication of a specific medical condition.

In order to mitigate such problems, often a re-assessment of the initial image is performed by the radiologist. However, the localization of the finding and the execution of the measurement can be a time consuming and non-trivial task.

An embodiment of a system is described herein that guides the radiologist through the review of an image. The system employs a report analyzer that receives a prior report and may use natural-language processing (NLP) techniques in order to identify relevant findings and measurements in the prior report. The system may also guide the radiologist to review the previous exam. Next, the system guides the radiologist to the region of interest in the prior medical image and triggers an automated measurement or measurement using CAD solutions. Next, the new image is analyzed using the same automated measurement or CAD solutions to provide a consistent measurement. This allows the visualization and re-assessment of the prior finding based upon the new image. Finally, the system employs a report generator that may use NLP techniques in order to produce new text to be added to the patient records.

Figure 1:
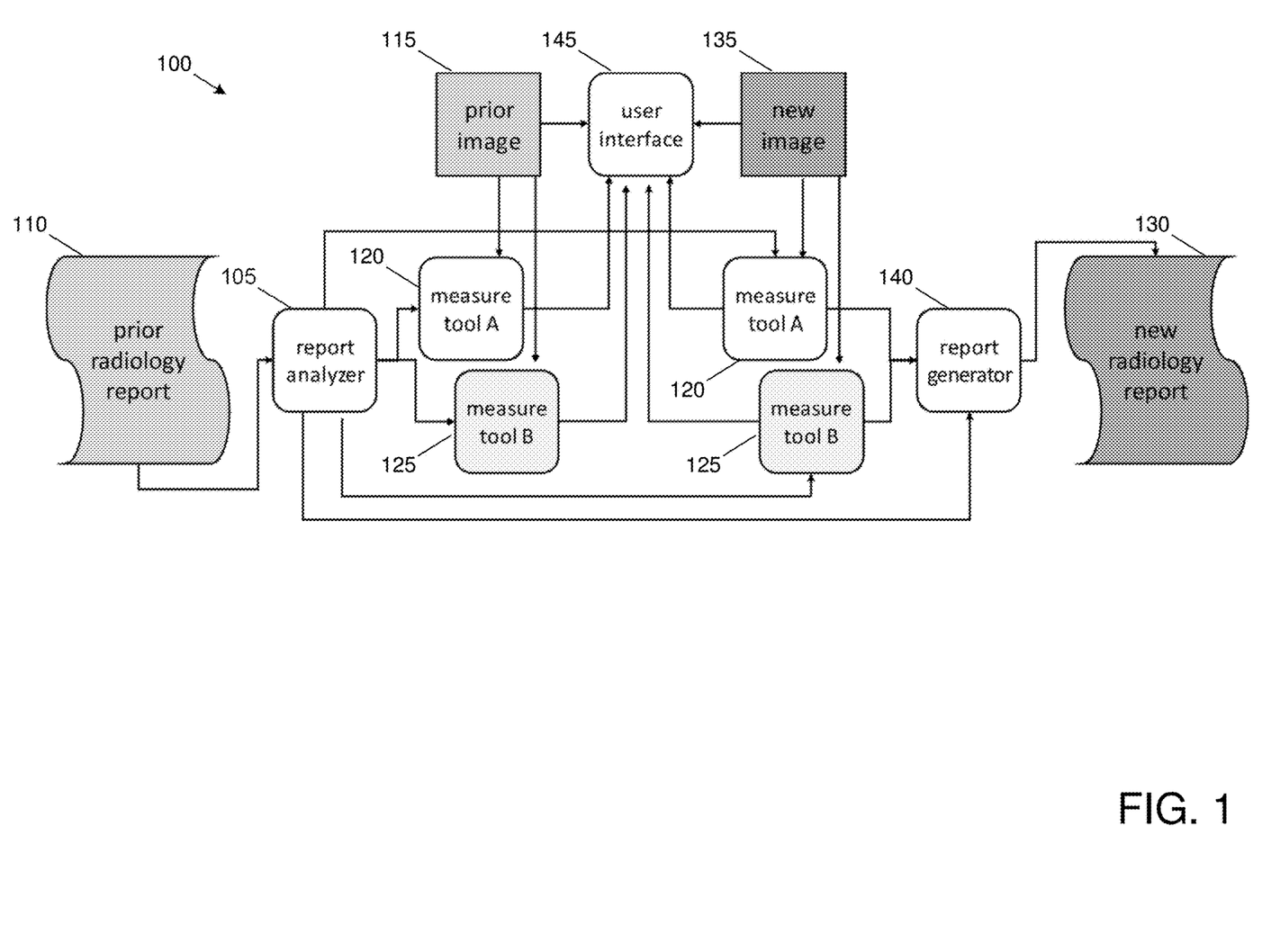
FIG. 1 illustrates a block diagram of an image diagnostic system.

FIG. 1 illustrates a block diagram of an image diagnostic system 100. The image diagnostic system includes a report analyzer 105, a measure tool A, a measure tool B, a report generator 140, and a user interface 145. The image diagnostic system 100 receives as inputs prior radiology report 110 and associated prior image and a new image 135 related to the prior image 115. In the following description of the image diagnostic system 100, the example of analyzing lung X-rays will be used to help explain the image diagnostic system 100, but any other type of medical image may be analyzed such as X-rays, sonograms, magnetic resonance imaging (MRI) images, etc. Further, the medical images may be two-dimensional (2D), three-dimensional (3D), or time series images.

Specifically, when a new image 135 to diagnose is received, the image diagnostic system 100 retrieves the related prior image 115 and prior report 110.

The report analyzer 105 may include an NLP engine which extracts the finding and related measurements from the prior report 110 associated with the prior image 115. For example, if the report mentions lung cancer and that there is a tumor that was previously measured to be 20 mm in size located in the upper right quadrant of the lung, this information is extracted from the report. Further, more than one finding and related measurement may be in the prior report. For example, if the report mentions pneumonia as well as the cancer, the opacity of the lung may also be measured to determine if the lung is clear. Any combination and number of findings may be extracted from the prior report. The NLP engine may be implemented using various different language processing technologies such as rule based engines, machine learning tools, etc.

In one embodiment the report analyzer 105 may be connected directly to a clinical report database. In other embodiments—to support interoperability between systems from different vendors—the report analyzer 105 may be accessed via drag-and-drop onto a text window or copying-and-pasting text into the text window.

After the NLP engine extracts the findings from the prior report 110, modules for the localization and assessment of the finding are triggered. The localization module may use information such as "the tumor is located in the upper right quadrant of the lung" in order to center the view of the prior image in the user interface 145. Also a visual indicator, e.g., a box. may be placed or draw around the region of interest. This eases the verification of the original measurements in the prior image by focusing on the area that the radiologist needs to measure. When there are multiple conditions to evaluate, both may be highlighted in some way, e.g., using two separate boxes using different colors around the areas of interest, to focus the radiologist to the portion(s) of the medical image needing evaluation. Alternatively, two different views may be made available to the radiologist where each highlights a specific condition, and the radiologist may switch between the views or the views may be presented side to side.

Next, the assessment module is used to facilitate the re-measurement of the prior measurement identified in the prior report 110. The assessment module identifies the specific measurement tools that are needed to perform the remeasurement. For example, if a cancer tumor measurement is needed, measure tool A is used to facilitate that measurement. If in addition the lungs were previously congested due to pneumonia, measure tool B may be used to measure the opacity of the lungs. The measure tools may be any type of tool such as a CAD tool. Such tools may make measurements automatically or may interact with a user to make the measurement. The tools may include various types of processing such as optical processing, geometric processing, classifiers, and machine learning models. The measure tools may perform various measurement, such as for example, length, width, diameter, area, volume, ratio, intensity, image opacity, shape, texture, bone age, tumor identification, classification, and measurement, flow measurement, perfusion measurement, uptake measurement, etc.

After the prior report 110 and prior image 115 have been analyzed and remeasured, the same measurements are performed using the same measurement tools 120 and 125 on the new image 135. This results in a consistent measurement of the prior image and the new image because the same measurement tools are used by the same radiologist.

The report generator 140 may include an NLP engine to generate report text for use in a new radiology report 130. The NLP engine may use various NLP techniques to produce this new report text. It may be as simple as having a set of templates that are available where the measurement information is inserted into the template. Such template may be customized for different users, practices, facilities, or some other characteristic. This allows for the report to match the desired format of the radiologist or other entity. The NLP engine may also use machine learning techniques for generating the new report text. Such NLP engine may be trained with prior relevant training data in order to produce the desired output. Further, the report analyzer 105 may produce information indicative of the style used in the prior report 110. This style information may be used by the report generator 140 to generate new report text in a style like that of the prior report. The style information may be a template in the case of a template based report generator 140 or machine learning features in a machine learning based report generator 140. The new report text may be automatically inserted into the prior report 110 to produce a new report 130. If such integration is not possible because of the use of legacy systems, the new report text may be presented to the radiologist who can then insert the new report text into the new report 130 using, for example, cut and paste or drag and drop functions.

The user interface 145 may then be used to present various information to the radiologist for consideration and action. During the re-measurement of the prior image 115, the prior image 115 may be presented to the radiologist with the prior report information and an indication of the regions of interest. When measurement tools requiring radiologist input are used, then such tools are used with the user interface 145 to facilitate the re-measurement of the prior image 115. Such re-measurement values may then be presented to the radiologist on the user interface 145. Further, the new mage may also be presented to the radiologist so that the new measurement may be made using the same measure tools as the re-measurement and the new measurement information may be displayed on the user interface 145. This may be done by using the whole user interface or side by side with the prior image 115 also on the user interface 145. Once, both measurements have been taken, the user interface 145 may present the images side by side for easy comparison along with the measured information for each image. Further, the image diagnostic system 100 may compare and analyze the two measurements to determine, for example, the progression of a disease. Such information may also be presented on the user interface 145. Also, such comparison information may also be included in the new text information added to the new report 130.

Figure 2:
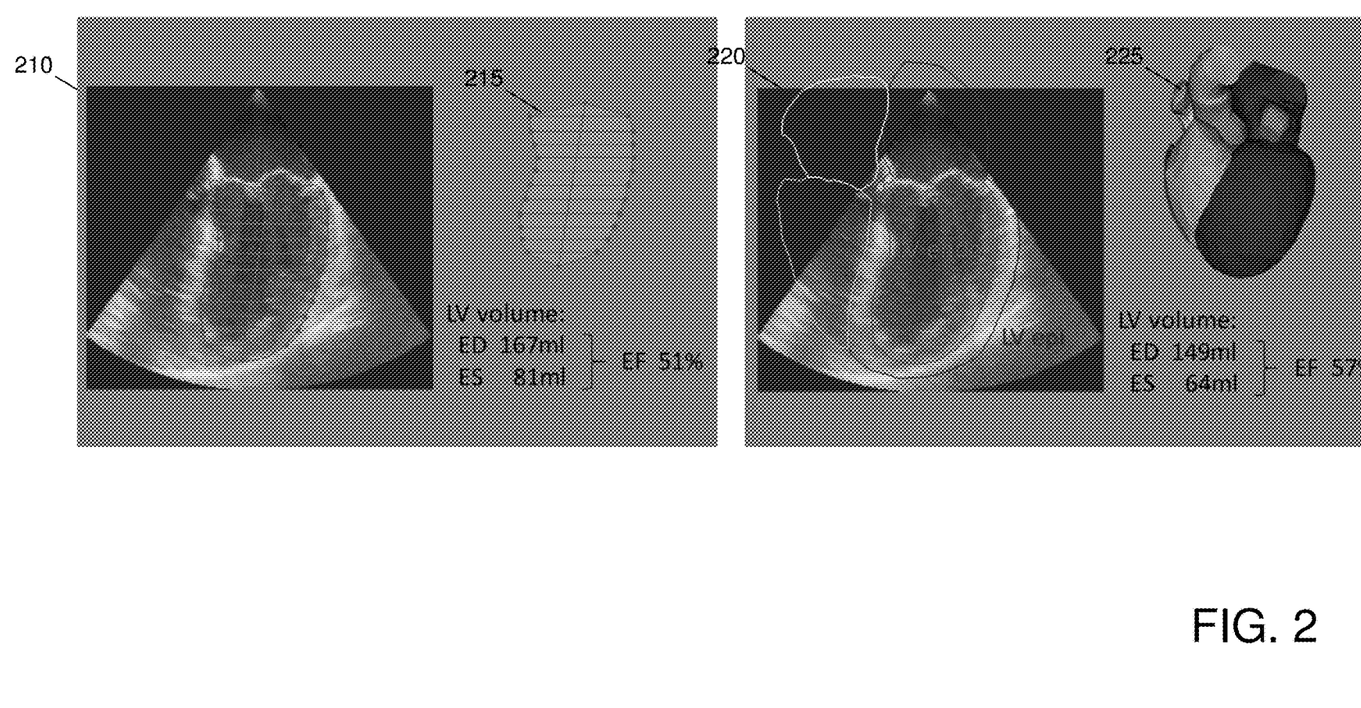
FIG. 2 illustrates an example of a re-measurement of a of a left-ventricular ejection fraction (EF) in a sonogram.

FIG. 2 illustrates an example of a re-measurement of a of a left-ventricular ejection fraction (EF) in a sonogram. The prior case 210 has been measured via Simpson's method shown as 215. The measured value is 51%. The re-measurement of the prior image 220 uses a three-dimensional heart model 225 to measure EF. In this case the heart model re-measurement determines an EF of 57%. In this case the prior case is automatically re-evaluated using the heart model to allow comparison to the new case (not shown). In this example, other types of measurements may include:

width, diameter, area, volume, intensity, opacity, uptake, perfusion, flow, shape, etc.

Figure 3:
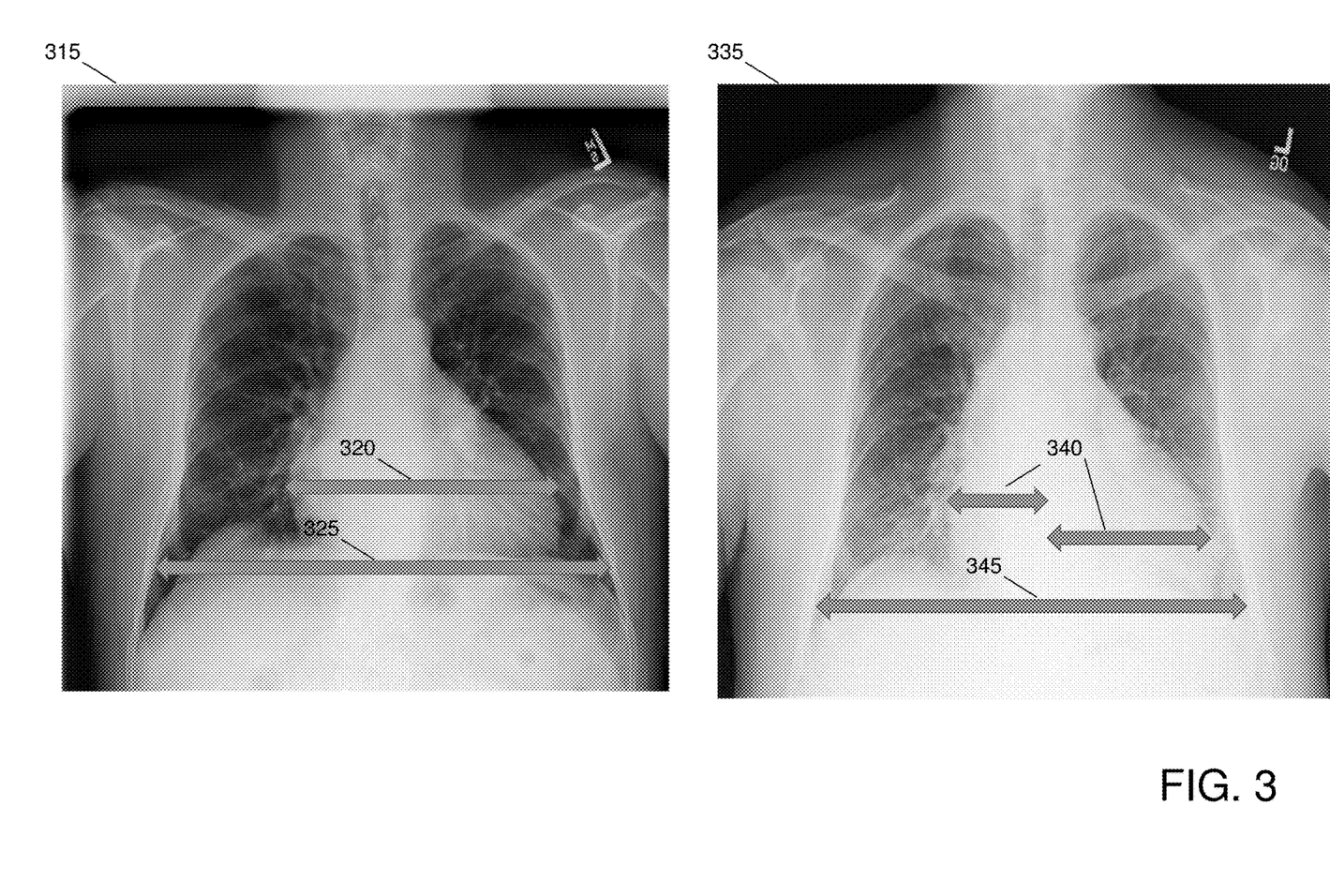
FIG. 3 illustrates an example of a re-measurement of cardiothoracic ratio (CRT) in a prior image and the measurement of CRT in a new image.

FIG. 3 illustrates the need for re-measurement of cardiothoracic ratio (CRT) in a prior image given a new image. In the prior image 315, a measurement of the width of the thoracic region 325 and the heart 320 was taken in a previous session using a measurement tool. As previously described, this may be done automatically or with the input and assistance of a radiologist. The same measurement tool is used to measure and calculate the CRT for a new image 335. For the new image, a measurement of the width of the thoracic region 345 is taken along with a measurement of the heart 340. Because of variability in tools and radiologists, the re-measurement is needed to provide consistency with the new measurement, which results in a better determination of changes in the patient's condition or the progression of disease in a patient.

Figure 4:
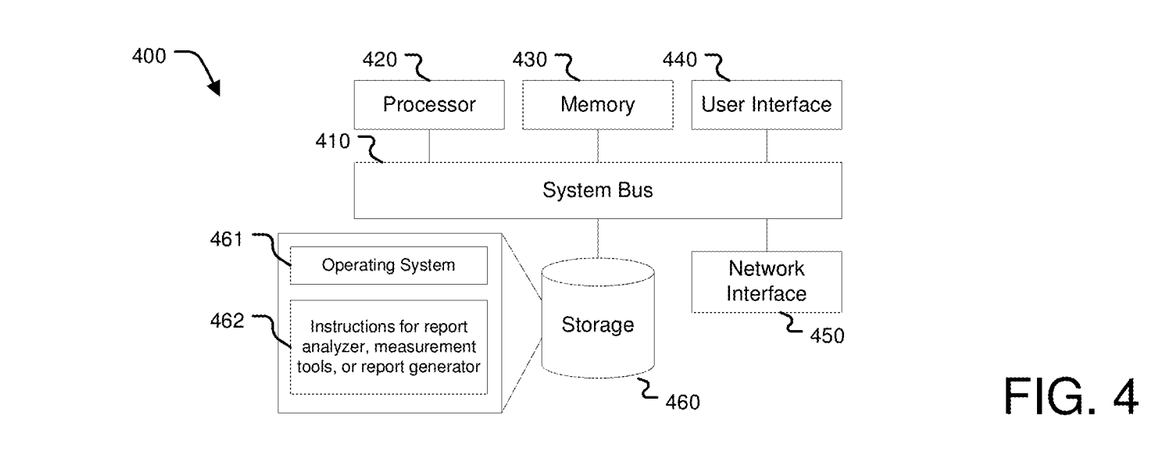
FIG. 4 illustrates an exemplary hardware diagram 400 for implementing a report analyzer, measurement tool, report generator, or the complete image diagnostic system.

The embodiments described above may be employed as part of a diagnostic image viewer or in the context of a more advanced diagnostic workstation. FIG. 4 illustrates an exemplary hardware diagram 400 for implementing a report analyzer, measurement tool, report generator, or the complete image diagnostic system. As shown, the device 400 includes a processor 420, memory 430, user interface 440, network interface 450, and storage 460 interconnected via one or more system buses 410. It will be understood that FIG. 4 constitutes, in some respects, an abstraction and that the actual organization of the components of the device 400 may be more complex than illustrated.

The processor 420 may be any hardware device capable of executing instructions stored in memory 430 or storage 460 or otherwise processing data. As such, the processor may include a microprocessor, a graphics processing unit (GPU), field programmable gate array (FPGA), application-specific integrated circuit (ASIC), any processor capable of parallel computing, or other similar devices.

The memory 430 may include various memories such as, for example L1, L2, or L3 cache or system memory. As such, the memory 430 may include static random-access memory (SRAM), dynamic RAM (DRAM), flash memory, read only memory (ROM), or other similar memory devices.

The user interface 440 may include one or more devices for enabling communication with a user including the user interface 145. For example, the user interface 440 may include a display, a touch interface, a mouse, and/or a keyboard for receiving user commands. In some embodiments, the user interface 440 may include a command line interface or graphical user interface that may be presented to a remote terminal via the network interface 450.

The network interface 450 may include one or more devices for enabling communication with other hardware devices. For example, the network interface 450 may include a network interface card (NIC) configured to communicate according to the Ethernet protocol or other communications protocols, including wireless protocols. Additionally, the network interface 450 may implement a TCP/IP stack for communication according to the TCP/IP protocols. Various alternative or additional hardware or configurations for the network interface 450 will be apparent.

The storage 460 may include one or more machine-readable storage media such as read-only memory (ROM), random-access memory (RAM), magnetic disk storage media, optical storage media, flash-memory devices, or similar storage media. In various embodiments, the storage 460 may store instructions for execution by the processor 420 or data upon with the processor 420 may operate. For example, the storage 460 may store a base operating system 461 for controlling various basic operations of the hardware 400. The storage 460 may store instructions 462 for the report analyzer, measurement tools, or report generator.

It will be apparent that various information described as stored in the storage 460 may be additionally or alternatively stored in the memory 430. In this respect, the memory 430 may also be considered to constitute a "storage device" and the storage 460 may be considered a "memory." Various other arrangements will be apparent. Further, the memory 430 and storage 460 may both be considered to be "non-transitory machine-readable media." As used herein, the term "non-transitory" will be understood to exclude transitory signals but to include all forms of storage, including both volatile and non-volatile memories.

While the host device 400 is shown as including one of each described component, the various components may be duplicated in various embodiments. For example, the processor 420 may include multiple microprocessors that are configured to independently execute the methods described herein or are configured to perform steps or subroutines of the methods described herein such that the multiple processors cooperate to achieve the functionality described herein. Further, where the device 400 is implemented in a cloud computing system, the various hardware components may belong to separate physical systems. For example, the processor 420 may include a first processor in a first server and a second processor in a second server.

The image diagnostic system described herein helps to improve the consistency between different measurement in medical images. This results in better tracking and determination of the condition of patients and the progression of their condition. Further, the image diagnostic system improves the re-measurement system by identifying the conditions present in a prior report and by then determining what area of an image to focus on and by determining which measurement tools to use to perform the re-measurement. Then the same measurement tools are used to measure the new medical image, thus resulting in the reduction in variations of measurement that result between different radiologists and different measurement tools. Further, the extraction of the findings or condition and location of interest from the prior report speeds up the remeasurement. In some cases the measurements may be made automatically for the radiologist, and the radiologist simply needs to verify the measurements. This also leads to less time being spent on re-measurement and comparison of measurements, which leads to increased radiologist throughput.

Any combination of specific software running on a processor to implement the embodiments of the invention, constitute a specific dedicated machine.

As used herein, the term "non-transitory machine-readable storage medium" will be understood to exclude a transitory propagation signal but to include all forms of volatile and non-volatile memory.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

The invention claimed is:

1. A system for reviewing a prior medical image and a related prior medical report, comprising:
a plurality of measurement tools including at least a size measurement tool and an opacity measurement tool, the plurality of measurement tools configured to:
receive the prior medical image and information regarding a medical finding;
analyze the prior medical image to determine a size measurement relating to the medical finding using the size measurement tool;
analyze the prior medical image to determine an opacity measurement relating to the medical finding using the opacity measurement tool; and
output the measurement relating to the medical finding;
a report analyzer configured to:
receive the prior radiology report;
analyze the prior radiology report to extract first information regarding a first medical finding described in the prior radiology report;
select one of the size and opacity measurement tools to analyze the prior medical image based upon the first extracted information; and
output the first extracted information to the first measurement tool, wherein the selected measurement tool remeasures the prior medical image to produce a first updated measurement of the first medical finding and the same selected measurement tool measures a new medical image associated with the prior medical image to produce a new first measurement of the first medical finding;
a report generator configured to:
receive the new first measurement of the first medical finding and the first updated measurement of the first medical finding; and
produce a new radiology report including inserting new report text containing the first updated measurement of the first medical finding and the new first measurement of the first medical finding into the new radiology report; and
a graphical user interface configured to display the new radiology report including the inserted new report text containing the first updated measurement of the first medical finding and the new first measurement of the first medical finding, and further configured to display the prior radiology report, the prior medical image, and the new medical image.

2. The system of claim 1, wherein the report analyzer includes a natural language processing engine and wherein the report generator includes a natural language processing engine.

3. The system of claim 1, wherein the report generator further receives style information from the report analyzer and the new radiology report has the same style as the prior radiology report.

4. The system of claim 1, wherein the report analyzer is further configured to:
analyze the prior radiology report to extract second information regarding a first medical finding described in the prior radiology report;
select the remaining measurement tool of the size and opacity measurement tools to analyze the prior medical image based upon the second extracted information; and
output the second extracted information to the second measurement tool,
wherein the selected remaining measurement tool analyzes the prior medical image to produce an updated second measurement of the first medical finding and the selected remaining measurement tool analyzes a new medical image associated with the prior medical image to produce a new second measurement of the first medical finding.

5. The system of claim 1, wherein the report analyzer is further configured to:
analyze the prior radiology report to extract second information regarding a second medical finding described in the prior radiology report;
select the remaining measurement tool of the size and replacement measurement tools to use to analyze the prior medical image based upon the extracted second information; and
output the second extracted information to the second measurement tool,
wherein the selected remaining measurement tool analyzes the prior medical image to produce an updated second measurement of the second medical finding and the selected remaining measurement tool analyzes a new medical image associated with the prior medical image to produce a new first measurement of the second medical finding.

6. The system of claim 1, wherein the first measurement tool uses one of machine learning and image processing to analyze the medical image.

7. The system of claim 1, wherein the graphical user interface is further configured to display condition progression information.

8. The system of claim 7, wherein the condition progression information comprises disease progression information.

9. The system of claim 1, wherein the size measurement tool facilitates interaction with the prior medical image.

10. The system of claim 1, wherein the size measurement tool is a CAD tool and the system is a radiology system.

11. A method for producing a new radiology report on a follow-up examination including automatically reviewing a prior medical image and a related prior radiology report, the method comprising:
receiving, by a report analyzer, the prior radiology report;
analyzing, by the report analyzer, the prior radiology report to extract first information regarding a first medical finding described in the prior radiology report;
using a size measurement tool to analyze the prior medical image based upon the first extracted information;
outputting the first extracted information to the size measurement tool;
remeasuring, by the size measurement tool, the prior medical image to produce a first updated measurement of the first medical finding;
measuring, by the size measurement tool, a new medical image associated with the prior medical image to produce a new first measurement of the first medical finding;
outputting, by the size measurement tool, both the new first measurement of the first medical finding and the first updated measurement of the first medical finding to a report generator; and producing, by the report generator, the new radiology report including inserting new report text containing the first updated measurement of the first medical finding and the new first measurement of the first medical finding into the new radiology report; and displaying, by a graphical user interface, the new radiology report including the inserted new report text containing the first updated measurement of the first medical finding and the new first measurement of the first medical finding, and further displaying the prior radiology report, the prior medical image, and the new medical image.

12. The method of claim 11, wherein the report analyzer is a natural language processing engine and wherein the report generator is a natural language processing engine.

13. The method of claim 11, wherein the report generator further receives style information from the report analyzer and the new radiology report has the same style as the prior radiology report.

14. The method of claim 11, further comprising, analyzing, by the report analyzer, the prior radiology report to extract second information regarding a first medical finding described in the prior radiology report;

using an opacity measurement tool to analyze the prior medical image based upon the second extracted information;

outputting the second extracted information to the opacity measurement tool;

analyzing, by the opacity measurement tool, the prior medical image to produce an updated second measurement of the first medical finding; and analyzing, by the second measurement, a new medical image associated with the prior medical image to produce a new second measurement of the first medical finding.

15. The method of claim 11, further comprising, analyzing, by the size measurement tool, the prior radiology report to extract second information regarding a second medical finding described in the prior radiology report;

using an opacity measurement tool to use to analyze the prior medical image based upon the extracted second information;

outputting the second extracted information to the opacity measurement tool, analyzing, by the opacity measurement tool, the prior medical image to produce an updated second measurement of the second medical finding; and analyzing, by the opacity measurement tool, a new medical image associated with the prior medical image to produce a new first measurement of the second medical finding.

16. The method of claim 11, wherein the first measurement tool uses one of machine learning and image processing to analyze the medical image.

17. The method of claim 11, further comprising:

determining condition progression information by analyzing the first updated measurement of the first medical finding and the new first measurement of the first medical finding; and displaying, by the graphical user interface, the condition progression information.

18. The method of claim 17, wherein the condition progression information comprises disease progression information.

19. The method of claim 11, wherein the size measurement tool comprises a user interface.

20. The method of claim 11, wherein the method is executed on a radiology system.

* * * * *